(12) United States Patent
Schramm et al.

(10) Patent No.: US 7,777,025 B2
(45) Date of Patent: Aug. 17, 2010

(54) TRANSITION STATE ANALOG INHIBITORS OF RICIN A-CHAIN

(75) Inventors: Vern L. Schramm, New Rochelle, NY (US); Richard Hubert Furneaux, Wellington (NZ); Peter Charles Tyler, Wellington (NZ); Gary Brian Evans, Lower Hutt (NZ)

(73) Assignees: Albert Einstein College of Medicine of Yeshiva University, Bronx, NY (US); Industrial Research Limited, Lower Hutt (NZ)

( * ) Notice: Subject to any disclaimer, the term of this patent is extended or adjusted under 35 U.S.C. 154(b) by 736 days.

(21) Appl. No.: 10/570,673

(22) PCT Filed: Sep. 9, 2004

(86) PCT No.: PCT/US2004/029491

§ 371 (c)(1),
(2), (4) Date: Jun. 11, 2007

(87) PCT Pub. No.: WO2005/023203

PCT Pub. Date: Mar. 17, 2005

(65) Prior Publication Data

US 2007/0269448 A1    Nov. 22, 2007

Related U.S. Application Data

(60) Provisional application No. 60/501,388, filed on Sep. 9, 2003.

(51) Int. Cl.
*A61K 6/00*    (2006.01)
(52) U.S. Cl. .................................... 536/27.6; 514/47
(58) Field of Classification Search .................. None
See application file for complete search history.

(56) References Cited

OTHER PUBLICATIONS

Tanaka et al (Biochem. 40: 6845-6851, 2001).*
Szewczak et al (Proc. Nat. Acad. Sci. USA 90: 9581-9585, 1993).*
Tanaka et al (Biochem 40: 6845-6851, 2001).*
Chen et al (JACS 122(28): 6527-6534, 2000).*
Orita et al (Nucl. Acids Res. 24(4): 611-618, 1996).*
Miller, D J et al., entitled "Structure-based design and characterization of novel platforms for ricin and shiga toxin inhibition," J Med Chem. Jan. 3, 2002;45(1):90-8.
Endo, Y et al., entitled "RNA-N-Glycosidase Activity of Ricin A-chain," The Journal of Biological Chemistry, vol. 262, No. 17, Issue of Jun. 15, 1987, 8128-8130.
Endo, Y et al., entitled "The RNA N-Glycosidase Activity of Ricin A-chain," The Journal of Biological Chemistry, vol. 263, No. 18, Issue of Jun. 25, 1988, 8735-8739.
Hesselberth, J R et al., entitled "In Vitro Selection of RNA Molecules that Inhibit the Activity of Ricin A-chain," The Journal of Biological Chemistry, vol. 275, No. 7, Issue of Feb. 18, 2000, 4937-4942.
Tanaka, K S E et al., entitled "Ricin A-Chain Inhibitors Resembling the Oxacarbenium Ion Transition State," Biochemistry 2001, 40, 6845-6851.
Yan, X et al., entitled "Structure-based identification of Ricin Inhibitor," J Mol Biol, 1997, 266, 1043-1049.
Notification of Transmittal of the International Search Report and the Written Opinion of the International Searching Authority, or the Declaration for PCT/US04/29491, Jul. 5, 2007, Albert Einstein College of Medicine of Yeshiva University and Industrial Research Limited.

* cited by examiner

*Primary Examiner*—Richard Schnizer
(74) *Attorney, Agent, or Firm*—Amster, Rothstein & Ebenstein LLP

(57) ABSTRACT

Improved transition state analog inhibitors of ricin toxin-A are provided. Methods of using those inhibitors to inhibit ricin toxin-A and to prevent the toxic effects of ricin toxin-A in a mammal are also provided.

18 Claims, 16 Drawing Sheets

FIG. 1

DADMe-A

```
                       SEQUENCE LISTING

<160> NUMBER OF SEQ ID NOS: 6

<210> SEQ ID NO 1
<211> LENGTH: 10
<212> TYPE: RNA
<213> ORGANISM: Artificial
<220> FEATURE:
<223> OTHER INFORMATION: ricin toxin-A inhibitor
<220> FEATURE:
<221> NAME/KEY: misc_feature
<222> LOCATION: (5)..(5)
<223> OTHER INFORMATION: n at 5 is an adenosine analog

<400> SEQUENCE: 1 cgcgngagcg                                                              10

<210> SEQ ID NO 2
<211> LENGTH: 10
<212> TYPE: RNA
<213> ORGANISM: Artificial
<220> FEATURE:
<223> OTHER INFORMATION: ricin toxin-A inhibitor
<220> FEATURE:
<221> NAME/KEY: misc_feature
<222> LOCATION: (4)..(4)
<223> OTHER INFORMATION: n at 4 is G or dG, where at least n at 4 or 6
      is dG
<220> FEATURE:
<221> NAME/KEY: misc_feature
<222> LOCATION: (5)..(5)
<223> OTHER INFORMATION: n at 5 is an adenosine analog
<220> FEATURE:
<221> NAME/KEY: misc_feature
<222> LOCATION: (6)..(6)
<223> OTHER INFORMATION: n at 6 is G or dG, where at least n at 4 or 6
      is dG

<400> SEQUENCE: 2 cgcnnnagcg                                                              10

<210> SEQ ID NO 3
<211> LENGTH: 14
<212> TYPE: RNA
<213> ORGANISM: Artificial
<220> FEATURE:
<223> OTHER INFORMATION: ricin toxin-A inhibitor
<220> FEATURE:
<221> NAME/KEY: misc_feature
<222> LOCATION: (6)..(6)
```

-continued

```
<223> OTHER INFORMATION: n at 6 is G or dG, where at least n at 6 or 8
      is dG
<220> FEATURE:
<221> NAME/KEY: misc_feature
<222> LOCATION: (7)..(7)
<223> OTHER INFORMATION: n at 7 is an adenosine analog
<220> FEATURE:
<221> NAME/KEY: misc_feature
<222> LOCATION: (8)..(8)
<223> OTHER INFORMATION: n at 8 is G or dG, where at least n at 6 or 8
      is dG

<400> SEQUENCE: 3
cgcgcnnnag cgcg                                                        14

<210> SEQ ID NO 4
<211> LENGTH: 10
<212> TYPE: RNA
<213> ORGANISM: Artificial
<220> FEATURE:
<223> OTHER INFORMATION: ricin toxin-A inhibitor
<220> FEATURE:
<221> NAME/KEY: misc_feature
<222> LOCATION: (4)..(4)
<223> OTHER INFORMATION: n at 4 is dG
<220> FEATURE:
<221> NAME/KEY: misc_feature
<222> LOCATION: (5)..(5)
<223> OTHER INFORMATION: n at 5 is an adenosine analog

<400> SEQUENCE: 4 cgcnngagcg                                                             10

<210> SEQ ID NO 5
<211> LENGTH: 10
<212> TYPE: RNA
<213> ORGANISM: Artificial
<220> FEATURE:
<223> OTHER INFORMATION: ricin toxin-A inhibitor
<220> FEATURE:
<221> NAME/KEY: misc_feature
<222> LOCATION: (5)..(5)
<223> OTHER INFORMATION: n at 5 is an adenosine analog
<220> FEATURE:
<221> NAME/KEY: misc_feature
<222> LOCATION: (6)..(6)
<223> OTHER INFORMATION: n at 6 is dG

<400> SEQUENCE: 5 cgcgnnagcg                                                             10

<210> SEQ ID NO 6
<211> LENGTH: 10
<212> TYPE: RNA
<213> ORGANISM: Artificial
<220> FEATURE:
<223> OTHER INFORMATION: ricin toxin-A inhibitor
<220> FEATURE:
<221> NAME/KEY: misc_feature
<222> LOCATION: (4)..(4)
<223> OTHER INFORMATION: n at 4 is dG
<220> FEATURE:
<221> NAME/KEY: misc_feature
<222> LOCATION: (5)..(5)
<223> OTHER INFORMATION: n at 5 is an adenosine analog
<220> FEATURE:
<221> NAME/KEY: misc_feature
```

```
<222> LOCATION: (6)..(6)
<223> OTHER INFORMATION: n at 6 is dG

<400> SEQUENCE: 6 cgcnnnagcg                                                          10
```

TRANSITION STATE ANALOG INHIBITORS OF RICIN A-CHAIN

CROSS-REFERENCE TO RELATED APPLICATIONS

This application is a national stage entry under 35 U.S.C. §371 of PCT International Application No. PCT/US2004/029491, filed Sep. 9, 2004, which claims the benefit of U.S. Provisional Patent Application No. 60/501,388, filed Sep. 9, 2003, the contents of which are incorporated herein by reference in their entirety.

STATEMENT OF GOVERNMENT SUPPORT

This invention was made with U.S. government support under grant number CA72444 awarded by the National Institutes of Health. The U.S. government has certain rights in the invention.

BACKGROUND OF THE INVENTION (1) Field of the Invention

The present invention generally relates to enzyme inhibitors. More specifically, the invention relates to improvements in the design of transition state analog inhibitors of ricin toxin-A, improved transition state analog inhibitors of ricin toxin-A, and methods of using those inhibitors.

(2) Description of the Related Art

REFERENCES CITED

Baluna R. et al., 1999, Proc. Natl. Acad. Sci. U.S.A. 96:3957-3962.
Endo, Y. et al., 1991, J. Mol. Biol. 221:193-207.
Engert, A et al., 1998, Curr. Top. Microbiol. Immunol. 234:13-33.
Hesselberth, J R et al., 2000, J. Biol. Chem. 275:4937-4942.
O'Toole, J E et al., 1998, Curr. Top. Microbiol. Immunol. 234:35-56.
Taneka, K S E et al., 2001, Biochemistry 40:6845-6851.
Wolfenden et al., 1992, Biochemistry 31:7356.
Yan, X et al., 1997, J. Mol. Biol. 266:1043-1049.

Ricin is a cytotoxic heterodimeric protein isolated from castor beans. The ricin toxin A-chain (RTA) is an N-glycosidase; it cleaves the C1'-N9 bond of a specific adenosine (A4324) which is the second residue in a 5'-GAGA-3' tetraloop secondary structural element on the 28S rRNA (FIG. 1). Hydrolysis of the adenosine results in a disruption in the ability of the 60S ribosomal subunit to bind elongation factors leading to inhibition of protein synthesis and cell death.

The B-chain is a galactose specific lectin that binds to cell surface receptors thus serving to direct the A-chain for internalization by receptor-mediated endocytosis (FIG. 2). It is then believed to be retrograde transported via the Golgi apparatus to the ER through the ERAD pathway. RTA is then exported to the cytosol via the Sec61p channel.

Ricin has very high mammalian toxicity, in the 82 g/kg range. As such, it has been used in political assassination and has been developed to be used as a terrorist weapon (see citations in Yan et al., 1997 and Hesselberth et al., 2000). RTA has also been covalently bound to antibodies to be utilized in the design of "magic bullet" immunotoxins, with considerable anticancer activity (Engert et al., 1998; O'Toole et al., 1998). However, nonspecific side effects limit its use (O'Toole et al., 1998; Baluna et al., 1999). Inhibitors of RTA are thus useful for their potential in preventing the acute toxic effects of ricin as well as the side effects of RTA immunotoxins.

Some RTA inhibitors have been developed, including structure-based inhibitors (Yan et al., 1997) and aptamers (Hesselberth et al., 2000). In another approach, inhibitors that resemble the oxacarbenium ion transition state of RTA were developed (Tanaka et al., 2001). This invention continues that approach, providing improved oligonucleotide analog inhibitors as well as novel small molecule inhibitors.

SUMMARY OF THE INVENTION

Accordingly, the present invention provides improvements in transition state inhibitors of ricin toxin-A.

Thus, in some embodiments, the invention is directed to transition state inhibitors of ricin toxin-A. The inhibitors comprise the sequence (d)GX(d)GA, where (d)G is either G or dG and X is an adenosine analog of the transition state of ricin toxin-A, where at least one of the (d)G moieties is a dG, and where any further nucleotide sequence extended from the sequence (d)GX(d)GA comprises a sequence of the stem loop structure flanking A4324 of the rat 28S rRNA. These inhibitors may also be in the form of a tautomer, a pharmaceutically acceptable salt, an ester, or a prodrug.

In other embodiments, the invention is directed to other transition state inhibitors of ricin toxin-A. These inhibitors comprise an adenosine analog (X) and stem loop structure of at least 9 ribonucleotides of the sequence CGCGXGAGCG (SEQ ID NO:1), where the transition state inhibitor also has the sequence of the stem loop structure flanking A4324 of the rat 28S rRNA, and where X is selected from the group consisting of BZ, PZ, and DA as provided in FIG. 9. These inhibitors may also be tautomers, pharmaceutically acceptable salts, esters, or prodrugs.

Additionally, the invention is directed to transition state inhibitors of ricin toxin-A comprising a pyrrolidine without additional ribonucleotides such as DADMe-A (FIG. 14). These inhibitors may also be tautomers, pharmaceutically acceptable salts, esters, or prodrugs.

In further embodiments, the invention is directed to a ricin toxin-A transition state inhibitor consisting of the compound of formula (I):

(I)

wherein:
Ad is adenin-9-yl;
Gu is guanine-9-yl;

$R^1$ is a 3'-linked RNA oligonucleotide of 1 to 10 alternating cytidine and guanosine nucleotide units;

$R^2$ is a 5'-linked RNA oligonucleotide of 1 to 10 alternating guanosine or cytidine nucleotide units;

V is selected from $CH_2$ and NH, and W is selected from $NR^1$ and $NR^2$; or V is selected from $NR^1$ and $NR^2$, and W is selected from $CH_2$ and NH;

X is selected from $CH_2$ and CHOH in the R or S-configuration, except where W is selected from NH, $NR^1$ and $NR^2$ then X is $CH_2$;

Y is selected from hydrogen, halogen and hydroxy, except where V is selected from NH, $NR^1$ and $NR^2$ then Y is hydrogen;

$Z^1$ and $Z^2$ are independently selected from hydrogen and hydroxyl; and $R^1$ is a radical of the formula (II)

(II)

$R^2$ is a radical of the formula (III)

(III)

wherein A is selected from N, CH and CR, where R is selected from halogen, optionally substituted alkyl, aralkyl or aryl, OH, $NH_2$, $NHR^3$, $NR^3R^4$ and $SR^5$, where $R^3$, $R^4$ and $R^5$ are each optionally substituted alkyl, aralkyl or aryl groups;

B is selected from $NH_2$, $NHR^6$, where $R^6$ is an optionally substituted alkyl, aralkyl or aryl group;

D is selected from OH, $NH_2$, $NHR^7$, hydrogen, halogen and $SCH_3$, where $R^7$ is an optionally substituted alkyl, aralkyl or aryl group;

E is selected from N and CH;

G is selected from $CH_2$, $CH_2CH_2$ and NH, or G is absent, provided that where W is $NR^1$ or $NR^2$ and G is NH then V is $CH_2$ and provided that where V is $NR^1$ or $NR^2$ and G is NH then W is $CH_2$.

As with the previously described inhibitors, these inhibitors may also be tautomers, pharmaceutically acceptable salts, esters, or prodrugs.

The present invention is also directed to methods of inhibiting ricin toxin-A. The methods comprise combining the ricin toxin-A with any of the transition state inhibitors described above.

Additionally, the invention is directed to methods of treating a mammal with a ricin toxin-A-antibody immunotoxin. The methods comprise treating the mammal with the ricin toxin-A-antibody immunotoxin and any of the transition state inhibitors described above.

BRIEF DESCRIPTION OF THE DRAWINGS

Figure 1:
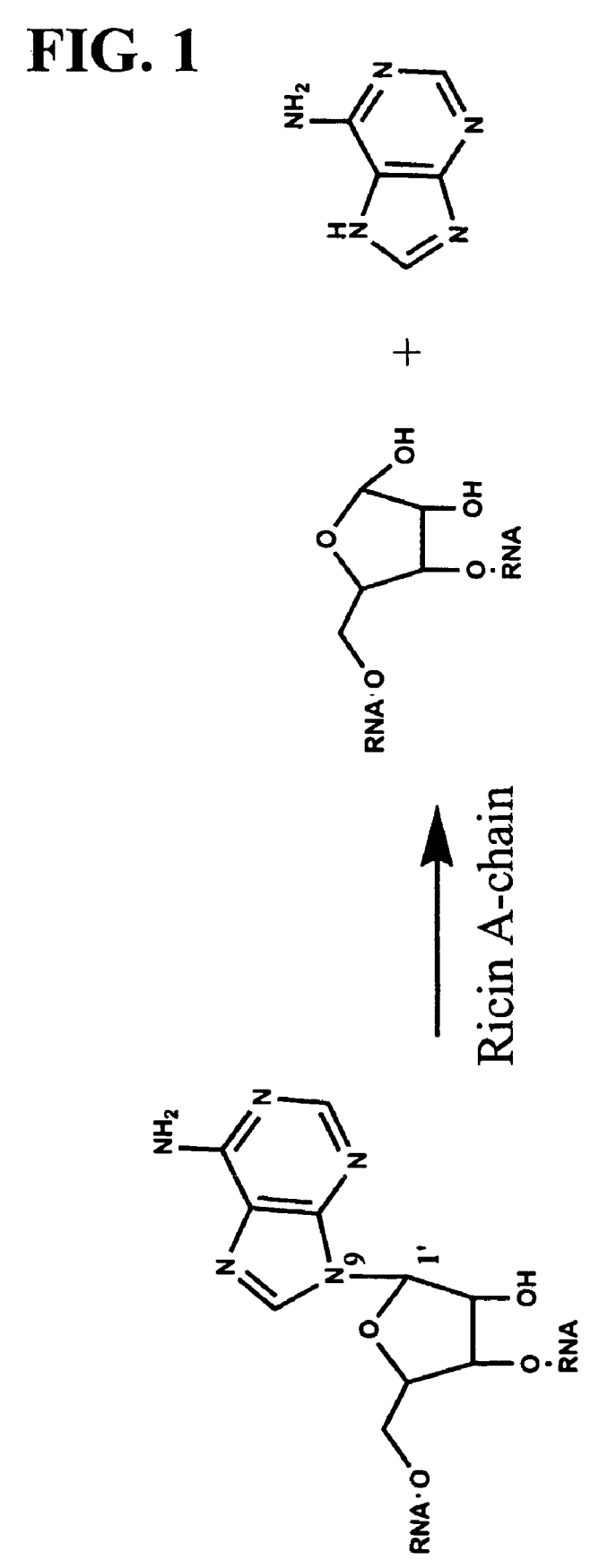

FIG. 1 provides the ricin toxin-A chemical reaction.

DETAILED DESCRIPTION OF THE INVENTION

The present invention provides improved transition state inhibitors of ricin toxin-A. These improved inhibitors were discovered based in part on the work described in the Example 1 elucidating the transition state of the RTA reaction.

In some embodiments, the invention is directed to transition state inhibitors of ricin toxin-A. These inhibitors comprise the sequence (d)GX(d)GA, where (d)G is either G or dG and X is an adenosine analog of the transition state of ricin toxin-A, where at least one of the (d)G moieties is a dG, and where any further nucleotide sequence extended from the sequence (d)GX(d)GA comprises a sequence of the stem loop structure flanking A4324 of the rat 28S rRNA (numbering as in GenBank Accession No. J10880, analogous to human 28S rRNA position A4565; the human sequence of the stem loop structure is homologous to the rat stem loop sequence). This stem loop sequence is called the Sarcin-Ricin loop of mammalian 28S rRNA.

As discovered in the research discussed in Example 1, a deoxyguanosine at the site preceding the depurination site, where the transition state analog substitutes for the adenine analogous to A4324 of the rat 28S rRNA (Endo et al., 1991), provides an improved inhibitor, as measured therein by a decreased $K_{cat}$ of the enzymatic reaction. The skilled artisan would understand that a deoxyguanosine after the depurination site, either substituting or in addition to the deoxyguanosine before the depurination site, would also provide improved inhibition to the transition state inhibitor. This improvement would also be expected with any adenosine substitution (X) that resembles the charge and geometry of the RTA transition state, for example P, IA, E, D, IR, IN, BZ, PZ, DA and DADMe-A as provided in FIGS. 6, 7, 9 and 14. It would also be understood that tautomers, pharmaceutically acceptable salts, esters, and prodrugs of these compounds would also be effective inhibitors, where the esters and prodrugs would be particularly useful in in vivo treatments to inhibit RTA toxicity. These tautomers, salts, esters and prodrugs could be prepared by the skilled artisan without undue experimentation.

In preferred embodiments, the sequence (d)GX(d)GA of the inhibitor is part of a stem loop structure having the sequence of the stem loop structure flanking A4324 of the rat 28S rRNA. Examples of these inhibitors comprise the sequence C(d)GX(d)GAG, CGC(d)GX(d)GAGCG (SEQ ID NO:2), CGCGC(d)GX(d)GAGCGCG (SEQ ID NO:3), CGCdGXGAGCG (SEQ ID NO:4), CGCGXdGAGCG (SEQ ID NO:5) or CGCdGXdGAGCG (SEQ ID NO:6).

Figure 16:
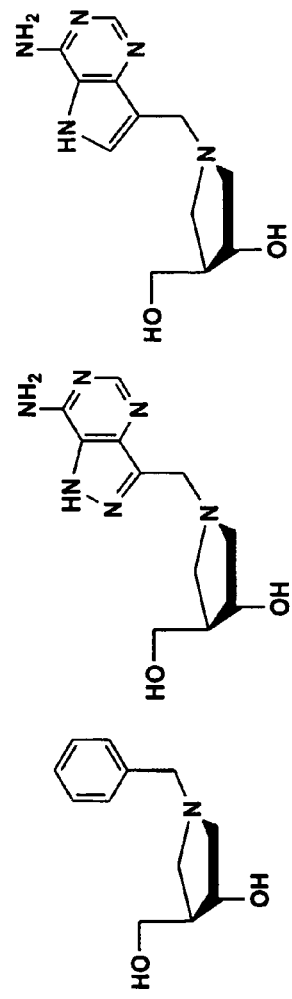
FIG. 16 shows compounds tested for RTA inhibitor activity.

In preferred embodiments, X is BZ, PZ or DA; in the most preferred embodiments, X is BZ. An example of a preferred inhibitor is BZ-5dG-10 of FIG. 16.

The present invention is also directed to additional transition state inhibitors of ricin toxin-A. These inhibitors comprise an adenosine analog (X) and stem loop structure of at least 9 ribonucleotides having the sequence CGCGXGAGCG (SEQ ID NO:1), where the transition state inhibitor also has the sequence of the stem loop structure flanking A4324 of the rat 28S rRNA, and where X is BZ, PZ, or DA as provided in FIGS. 9 and 14. As shown in the Example, the stem-loop structures BZ, PZ, and DA, by virtue of their similarity to the charge and geometry of the RTA transition state, inhibit RTA. Since DADMe-A provides inhibition without being incorporated into the stem-loop structure, the skilled artisan would understand that it would also provide inhibition when it is incorporated into the stem-loop structure. Tautomers, or a pharmaceutically acceptable salts, esters, and prodrugs of these inhibitors would, again, also provide effective RTA inhibition.

Figure 14:
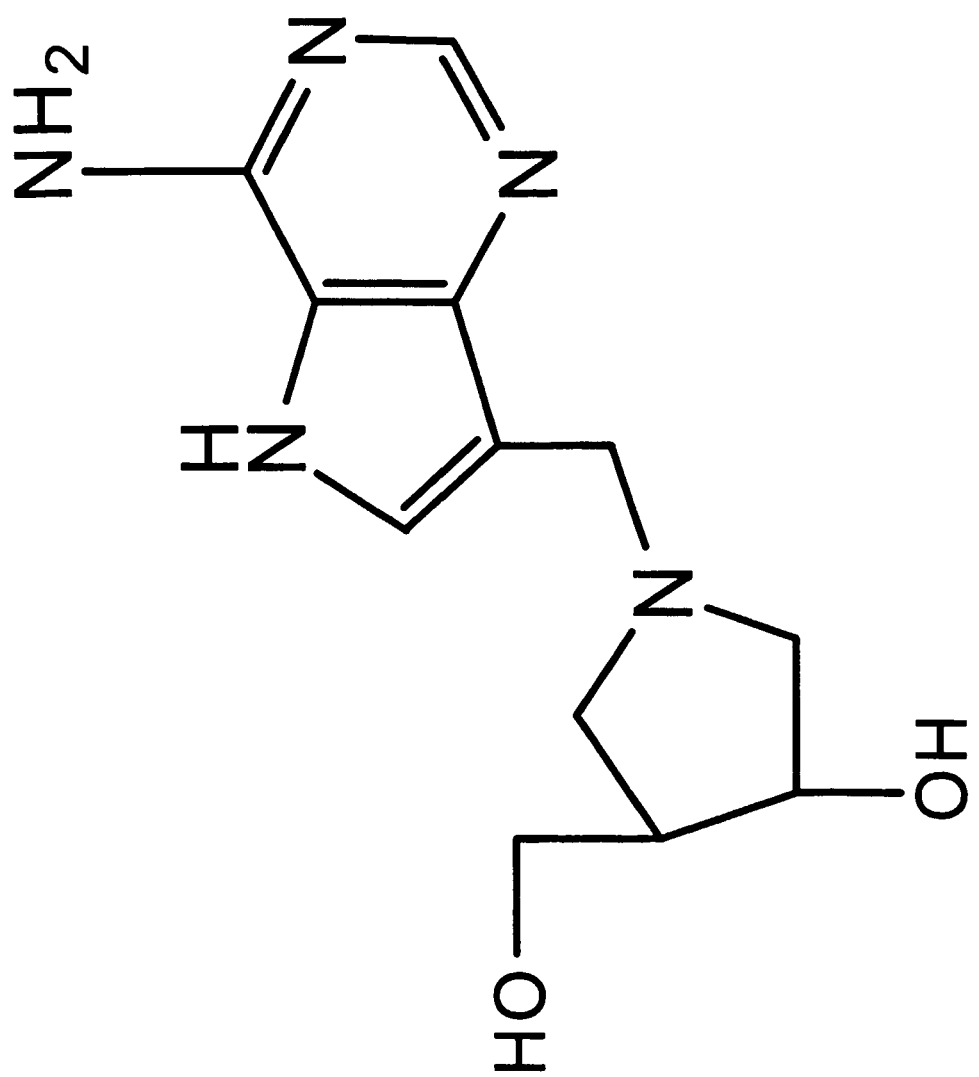
FIG. 14 shows the chemical structure of DADMe-A.

In further embodiments, the invention is directed to small molecule transition state inhibitors of ricin toxin-A. These small molecules are capable of inhibiting RTA without being incorporated into a stem-loop structure. These inhibitors comprise a pyrrolidine that has a similar charge and geometry of the RTA transition state. An example of these small molecule inhibitors is DADMe-A (FIG. 14). Tautomers, or a pharmaceutically acceptable salts, esters, and prodrugs of these inhibitors would also provide effective RTA inhibition, as with the inhibitors described above.

A preferred example of these pyrrolidine transition state inhibitors is DADMe-A, as provided in FIG. 14. These pyrrolidine transition state inhibitors, including DADMe-A, can optionally comprise a 3' phosphate, or a 5' phosphate, or both a 3' phosphate and a 5' phosphate, which would not be expected to prevent their inhibitory activity.

In additional embodiments, the invention is directed to additional transition state inhibitors of ricin toxin-A. These inhibitors consist of the compound of formula (I):

(I)

wherein:

Ad is adenin-9-yl;

Gu is guanine-9-yl;

$R^1$ is a 3'-linked RNA oligonucleotide of 1 to 10 alternating cytidine and guanosine nucleotide units;

$R^2$ is a 5'-linked RNA oligonucleotide of 1 to 10 alternating guanosine or cytidine nucleotide units;

V is selected from $CH_2$ and NH, and W is selected from $NR^1$ and $NR^2$; or V is selected from $NR^1$ and $NR^2$, and W is selected from $CH_2$ and NH;

X is selected from $CH_2$ and CHOH in the R or S-configuration, except where W is selected from NH, $NR^1$ and $NR^2$ then X is $CH_2$;

Y is selected from hydrogen, halogen and hydroxy, except where V is selected from NH, $NR^1$ and $NR^2$ then Y is hydrogen;

$Z^1$ and $Z^2$ are independently selected from hydrogen and hydroxyl; and $R^1$ is a radical of the formula (II)

(II)

$R^2$ is a radical of the formula (III)

(III)

wherein A is selected from N, CH and CR, where R is selected from halogen, optionally substituted alkyl, aralkyl or aryl, OH, $NH_2$, $NHR^3$, $NR^3R^4$ and $SR^5$, where $R^3$, $R^4$ and $R^5$ are each optionally substituted alkyl, aralkyl or aryl groups;

B is selected from $NH_2$, $NHR^6$, where $R^6$ is an optionally substituted alkyl, aralkyl or aryl group;

D is selected from OH, $NH_2$, $NHR^7$, hydrogen, halogen and $SCH_3$, where $R^7$ is an optionally substituted alkyl, aralkyl or aryl group;

E is selected from N and CH;

G is selected from $CH_2$, $CH_2CH_2$ and NH, or G is absent, provided that where W is $NR^1$ or $NR^2$ and G is NH then V is $CH_2$ and provided that where V is $NR^1$ or $NR^2$ and G is NH then W is $CH_2$.

Tautomers, or a pharmaceutically acceptable salts, esters, and prodrugs of these inhibitors are also envisioned as within the scope of the invention.

Any of the above-described RTA transition state inhibitors can be formulated in a pharmaceutically acceptable excipient, for pharmaceutical administration to a mammal, including humans. These formulations can be prepared for administration without undue experimentation for any particular application. The inhibitor compositions can also be prepared alone or in combination with other medications, such as chemotherapeutic agents. Additionally, proper dosages of the inhibitors can be determined without undue experimentation using standard dose-response protocols.

Accordingly, the inhibitor compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical inhibitor compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The inhibitor compositions of the present invention can easily be administered parenterally such as for example, by intravenous, intramuscular, intrathecal or subcutaneous injection, either alone or combined with another medication, e.g., a chemotherapeutic agent. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical inhibitor compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the inhibitor composition through the skin. Transdermal formulations include patches (such as the well-known nicotine patch), ointments, creams, gels, salves and the like.

The present invention includes nasally administering to the mammal a therapeutically effective amount of the inhibitor composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the composition may also take place using a nasal tampon or nasal sponge.

The present invention is also directed to methods of inhibiting ricin toxin-A. The methods comprise combining the ricin toxin-A with any of the above-described transition state inhibitors. In preferred embodiments, the ricin toxin-A is in a living mammalian cell, where the presence of the inhibitor in sufficient concentration would prevent the ricin toxin-A-induced death of the cell. These methods would be particularly useful in a cell that is in a living mammal, preferably a human, where the inhibitor could prevent serious illness or death of the mammal.

In one aspect of these methods, the mammal (e.g., human) is undergoing treatment with a ricin toxin-A-antibody immunotoxin, e.g., for cancer, where the inhibitor would be expected to prevent the nonspecific side effects that have plagued clinical trials with such "magic bullet" immunotoxins. See discussion in Background section above.

In another aspect of these methods, the inhibitor would be expected to counter an accidental or intentional ricin poisoning of the mammal, e.g., a cow that grazed on castor beans contaminating a field, or a human victim of a terrorist attack.

The invention is further directed to methods of treating a mammal with a ricin toxin-A-antibody immunotoxin. The methods comprise treating the mammal with any of the transition state inhibitors described above, in a pharmaceutically acceptable excipient. In preferred embodiments, the mammal is a human being treated for cancer with the immunotoxin. In these methods, it is preferred that the mammal is treated with the inhibitor either before or during the treatment with the immunotoxin, in order to achieve the maximal inhibitory effects.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1

Transition State Inhibitors of Ricin Toxin-A

Figure 2:
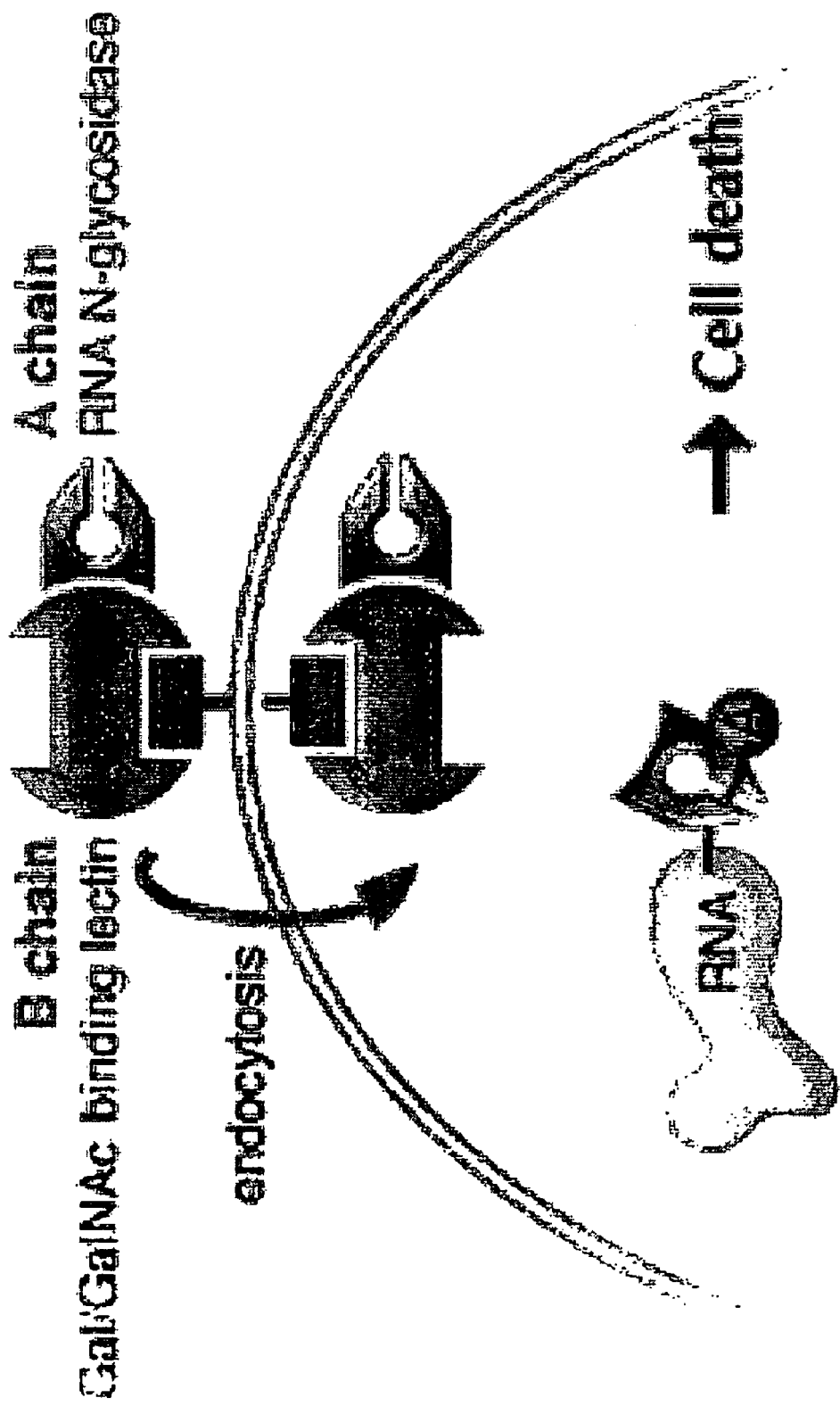
FIG. 2 is a cartoon showing the mechanism of action of ricin in a mammalian cell.
Figure 3:
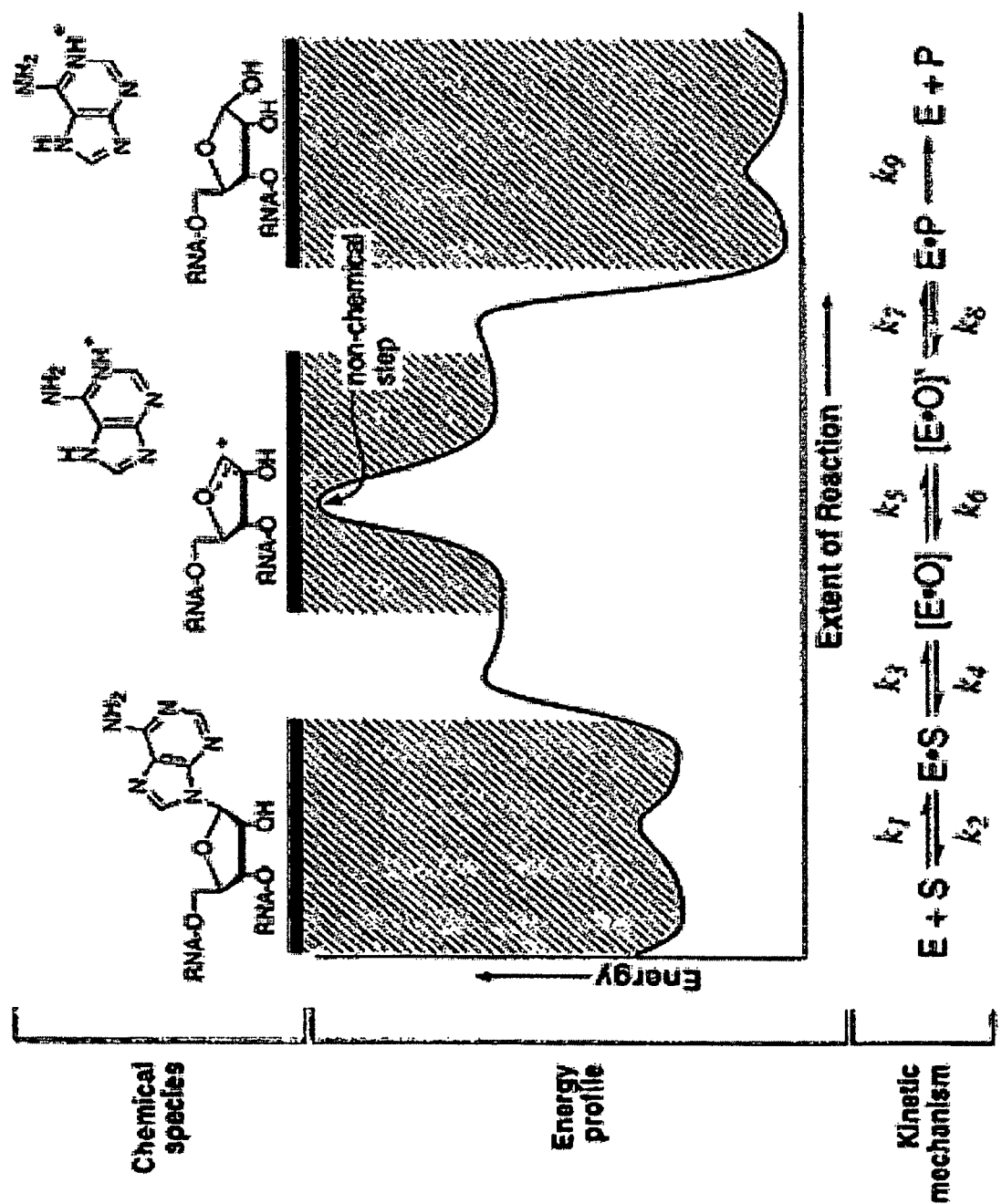
FIG. 3 is a graph of the kinetic mechanism of the ricin toxin-A chemical reaction.

Ricin A-Chain Catalytic Mechanism. Transition state inhibitor design requires the knowledge of the transition state of the reaction. Kinetic isotope effects were measured on the ricin toxin-S (RTA) hydrolytic reaction employing a 10mer stem-tetraloop type RNA oligonucleotide (labeled A-10 in FIG. 6) with the susceptible adenosine labeled with either $^{14}C$, $^{3}H$ or $^{15}N$ at different positions either on the ribose ring or on the adenine base. Equilibrium isotope effects were also calculated. The kinetic mechanism is shown in FIG. 3.

Figure 4:
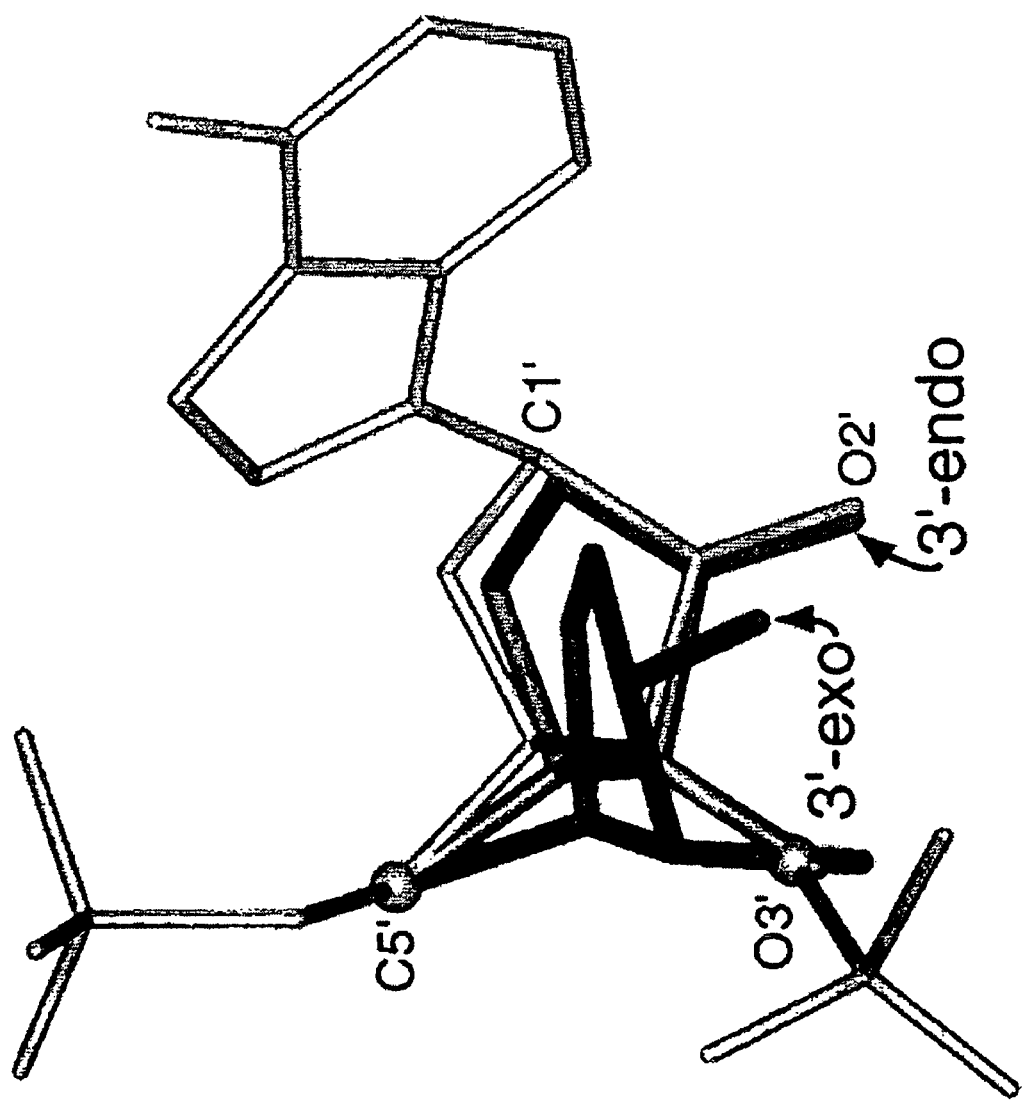
FIG. 4 is a stick figure of the superimposition of the X-ray structure of the scissile adenosine residue of the GAGA tetralopp (light gray) on the quantum mechanically optimized 3'-endo and 3'-exo confirmations of the oxacarbenium ion.

The experimental primary $1'$-$^{14}C$ KIE was inverse, which is inconsistent with traditional concerted (KIE~1.01) and stepwise (KIE~1.018) mechanisms for nucleophilic substitution. However, it is consistent with the calculated value of equilibrium isotope effect for an oxacarbenium ion intermediate ([E.O] in the kinetic scheme). EIE's were calculated for an equilibrium between a model compound, 2'-hydroxy-purine riboside and its 3'-endooxacarbenium ion. The structures in FIG. 4 show the superimposition of the X-ray structure of the scissile adenosine residue of the GAGA tetraloop (light gray) on the quantum mechanically optimized 3'-endo and 3'-exo conformations of the oxacarbenium ion. As seen from the figure, adoption of the 3'-exo conformation in the transition state would require major structural changes in the RNA backbone. $2'$-$^{3}H$ KIE of 1.012 supports a 3'-endo conformation based on a calculated p-orbital-C1'-C2'-H2' dihedral angle of 48°.

Figure 5:
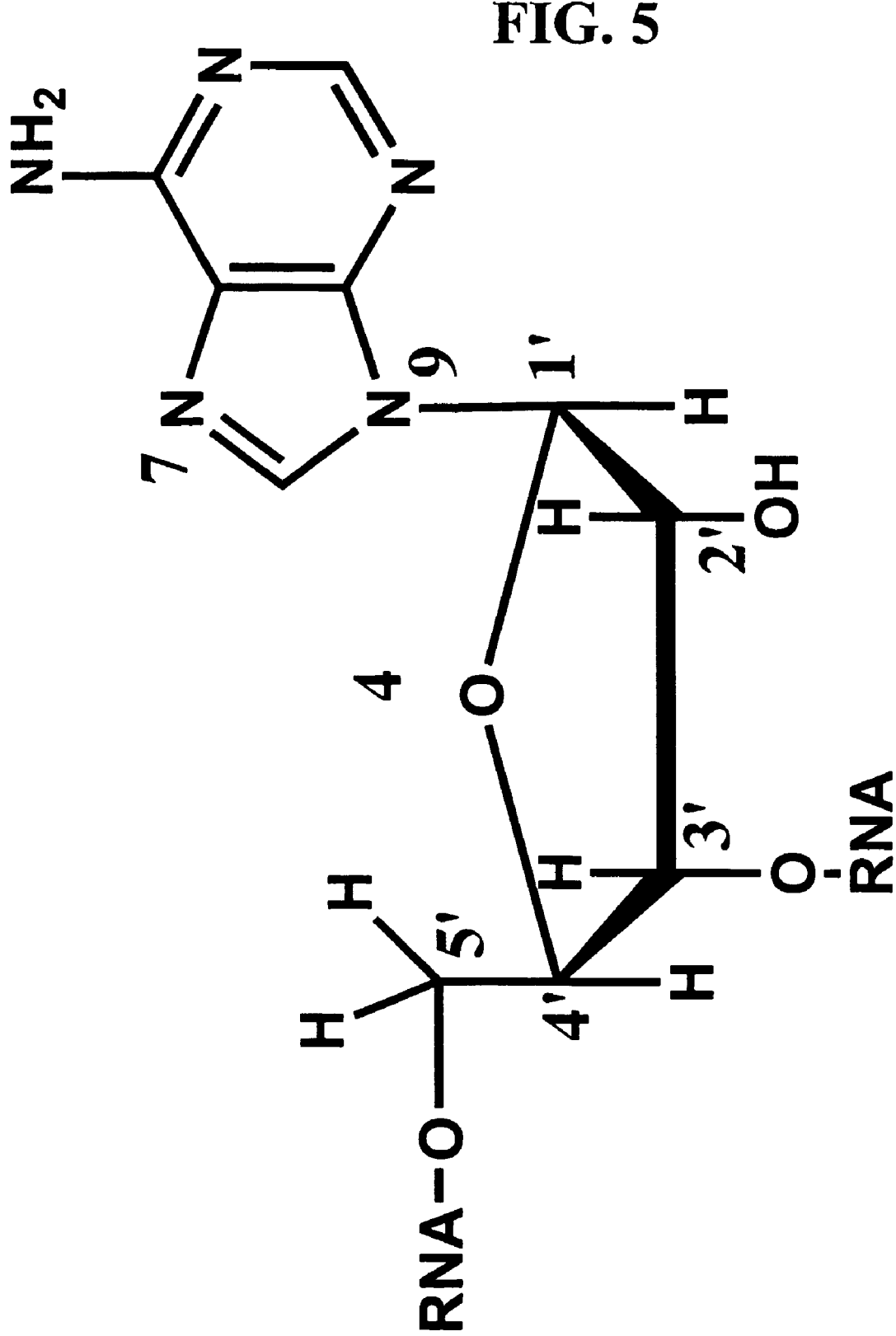
FIG. 5 shows the ricin toxin-A substrate with the numbered atoms that were subject to kinetic isotope effects (KIE) analysis.

These studies suggest a $D_N*A_N$ dissociative mechanism for the hydrolysis which proceeds via an oxacarbenium ion intermediate. The studies also suggest an unusual 3'-endo conformation in the enzyme bound oxacarbenium ion. See Table 1 for the experimental KIE values of the bonds identified in FIG. 5.

TABLE 1

| Experimental KIE's |
|---|
| $[1'$-$^{14}C]$~0.993 |
| $[1'$-$^{3}H]$~1.163 |
| $[9$-$^{15}N]$~1.012 |
| $[7$-$^{15}N]$~0.981 |
| $[2'$-$^{3}H]$~1.012 |

Figure 6:
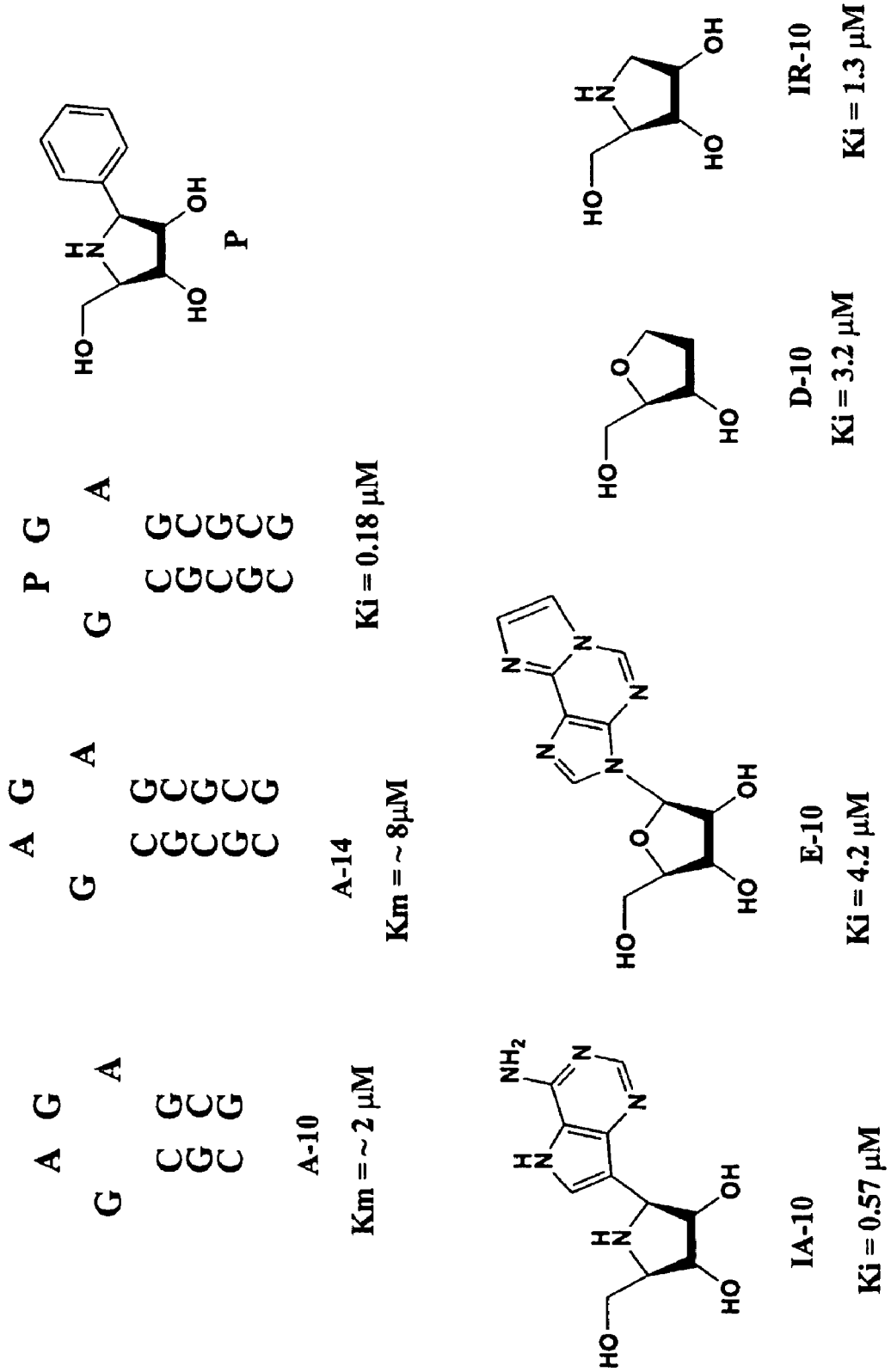
FIG. 6 shows several compounds that are substrates or inhibitors of ricin toxin-A, along with their $K_m$ (for substrates) or $K_i$ (for inhibitors) values. The $K_i$ values for IA-10, E-10, D-10, and IR-10 are the measured values for the compound shown when incorporated into the stem-loop of A-10 in place of the first A moiety in the loop (corresponding with A4324 of the 28S rRNA).
Figure 7:
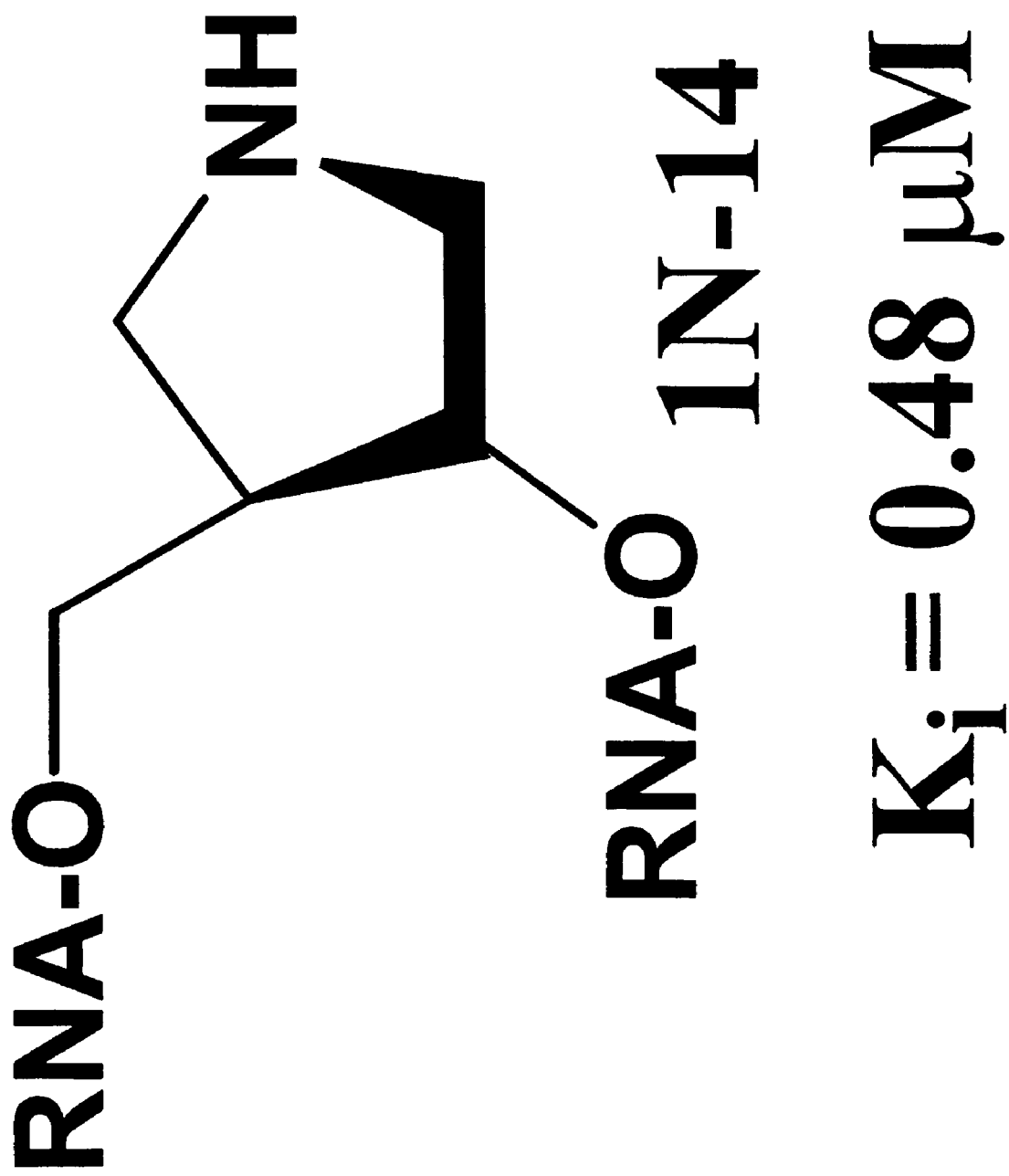
FIG. 7 shows the chemical structure of the inhibitor moiety that was incorporated into the stem-loop of A-14 in place of the first A moiety in the loop (corresponding with A4324 of the 28S rRNA) to create compound IN-14, along with the $K_i$ value of IN-14.

Ricin A-Chain Inhibition. Short stem loop RNA structures are substrates of ricin although the $k_{cat}$ of the hydrolytic reaction is much smaller (10-100 min$^{-1}$) compared to that of the intact ribosomes (1777 min$^{-1}$). Stem-loop RNA structures with modified adenosine analogs in the depurination site were conceived and synthesized as potential inhibitors of RTA. These are shown in FIG. 6. The transition state for the hydrolysis possesses two halves; an oxacarbenium ion half and a leaving group half. Stem-loop structures with nonnatural analogs in the depurination site mimic the transition state for adenosine hydrolysis: the ring nitrogen is thought to be protonated on the enzyme which gives it features of an oxacarbenium ion. RTA activates the leaving group for departure by protonation and the large inverse 7-$^{15}N$ KIE suggests that N7 is protonated in the transition state. This feature has been built into the inhibitors IA-10 and E-10 shown in FIG. 6. Also shown are the abasic inhibitors D-10 and IR-10 which are only able to capture binding energy from the oxacarbenium half of the transition state.

Inhibition: The 1-azasugars. The structures shown in FIG. 6 contain an iminoribitol moiety as a ribose isostere and an oxacarbenium ion mimic. Second generation inhibitors were then designed to improve binding affinities. These structures incorporate a polyhydroxypyrrolidine as the ribose isostere. The pyrrolidine is also a closer mimic of the oxacarbenium ion intermediate than the iminoribitol since the positive charge on the nitrogen resides where the positive charge on C1' would be in the transition state for substrate hydrolysis. An abasic analog 1N-14 is shown on the left and a comparison with IR-10 ($K_i$=1.3 µM), which incorporates an iminoribitol, shows that 1N-14 binds twice as good. Since both molecules are abasic, the differences in their affinities reflect differences in their ability to mimic the oxacarbenium ion half of the transition state.

Figure 8:
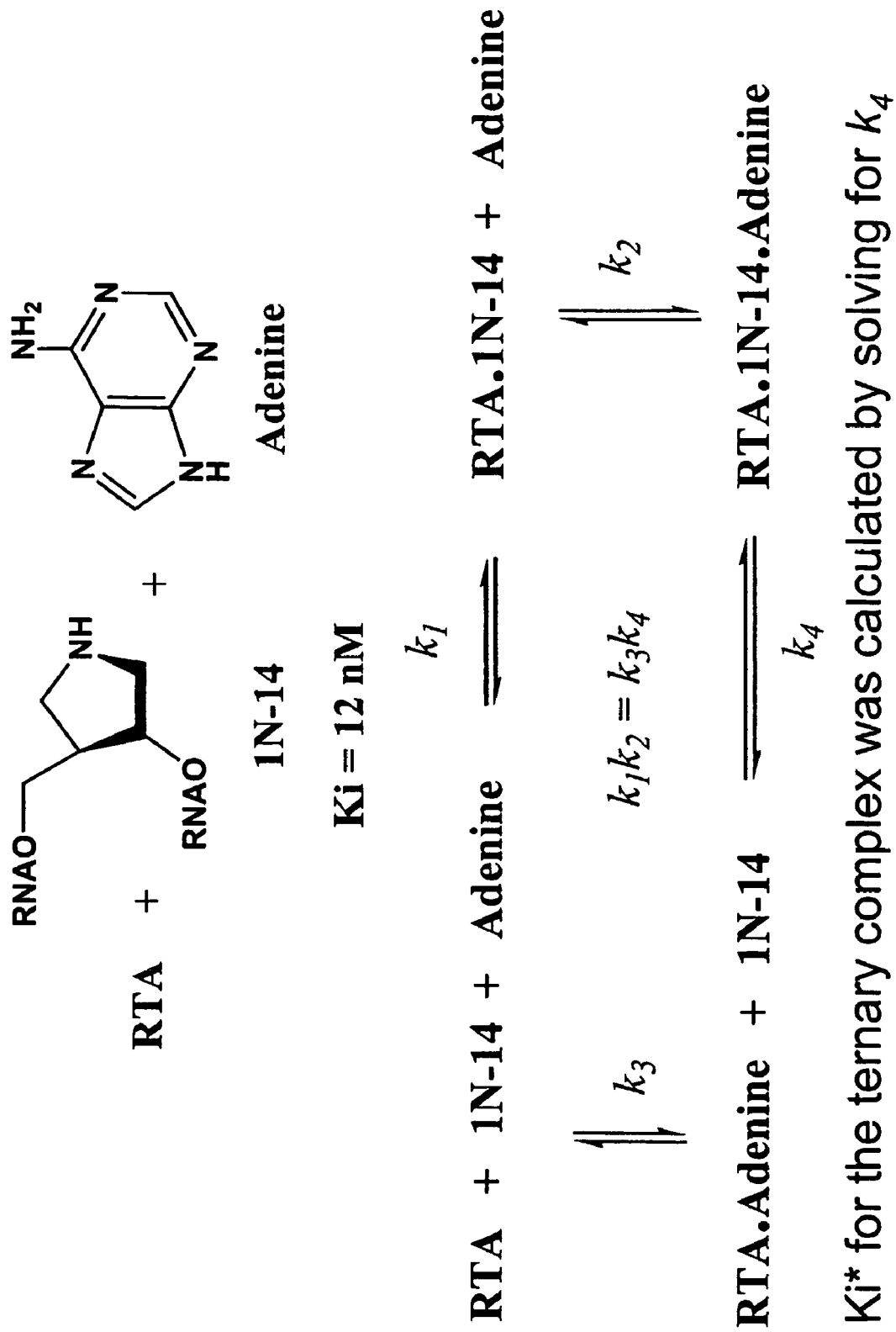
FIG. 8 shows the thermodynamic box of the IN-14-adenine-RTA ternary complex, used to calculate the $K_i$ for the ternary complex.

The next logical step was to incorporate features of the leaving group into the design. Inhibition of a ternary complex of RTA, 1N-14 and adenine that has both oxacarbenium ion character and features of the leaving group was studied. A $K_i$ of 12 nM was determined by fitting to a model described by the thermodynamic box shown in FIG. 8. This is the tightest binding known for RTA. Interestingly, a similar complex with 9-deazaadenine had a binding constant of 100 nM.

Inhibition: Towards a better capture of transition state energy. Wolfenden et al. (1992) have dissected the transition state analogues of adenosine deaminase and conclude that 7-10 kcal/mol can be gained from appropriate connectivity of fragments. Based on this hypothesis, the methylene bridge was incorporated into the 1-aza position of the pyrrolidine to satisfy: a) positive charge on N1 (mimic of the charge at C1' in the substrate and b) to mimic the distance between the reacting center (N1'/C1') and the leaving group. Table 2 shows the $K_i$ values of the different methylene bridged compounds that were synthesized (FIG. 9).

TABLE 2

Figure 9:
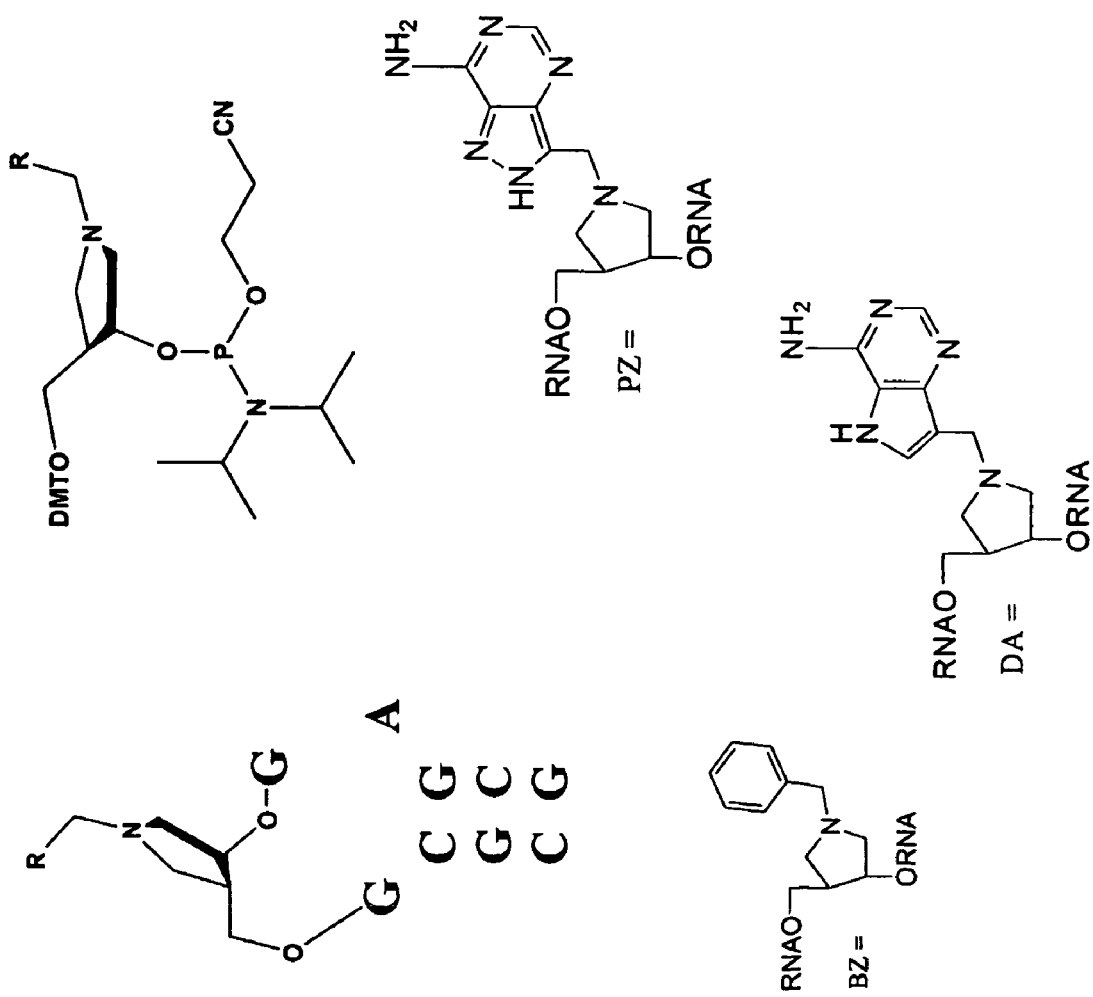
FIG. 9 shows the chemical structures of BZ, DA, and PZ, which substitute for adenosine in transition state inhibitors of the present invention.

| $K_i$ values of compounds shown in FIG. 9, and comparisons with 1N-14. | | |
|---|---|---|
| | | Relative affinity to 1N-14 |
| Inhibitor | $K_i$ (µM) | Without Adenine | With Adenine |
| BZ-10 | 0.099 ± 0.013 | 4.8 | 0.16 |
| BZ-14 | 0.682 ± 0.093 | 0.7 | 0.017 |
| PZ-10 | 0.163 ± 0.008 | 3 | 0.07 |

TABLE 2-continued $K_i$ values of compounds shown in FIG. 9, and comparisons with 1N-14.

| | | Relative affinity to 1N-14 | |
|---|---|---|---|
| Inhibitor | $K_i$ (μM) | Without Adenine | With Adenine |
| PZ-14 | 0.094 ± 0.007 | 5 | 0.12 |
| DA-10 | 0.280 ± 0.004 | 1.7 | 0.04 |

The modified bases were incorporated into a stem loop RNA structure using the standard phosphoramidite coupling protocol on an automated DNA/RNA synthesizer. The oligos were purified by RP HPLC and analyzed by MALDI mass spectrometry and composition analysis was performed on HPLC after enzymatic digestion with snake venom phosphodiesterase and alkaline phosphatase.

Figure 10:
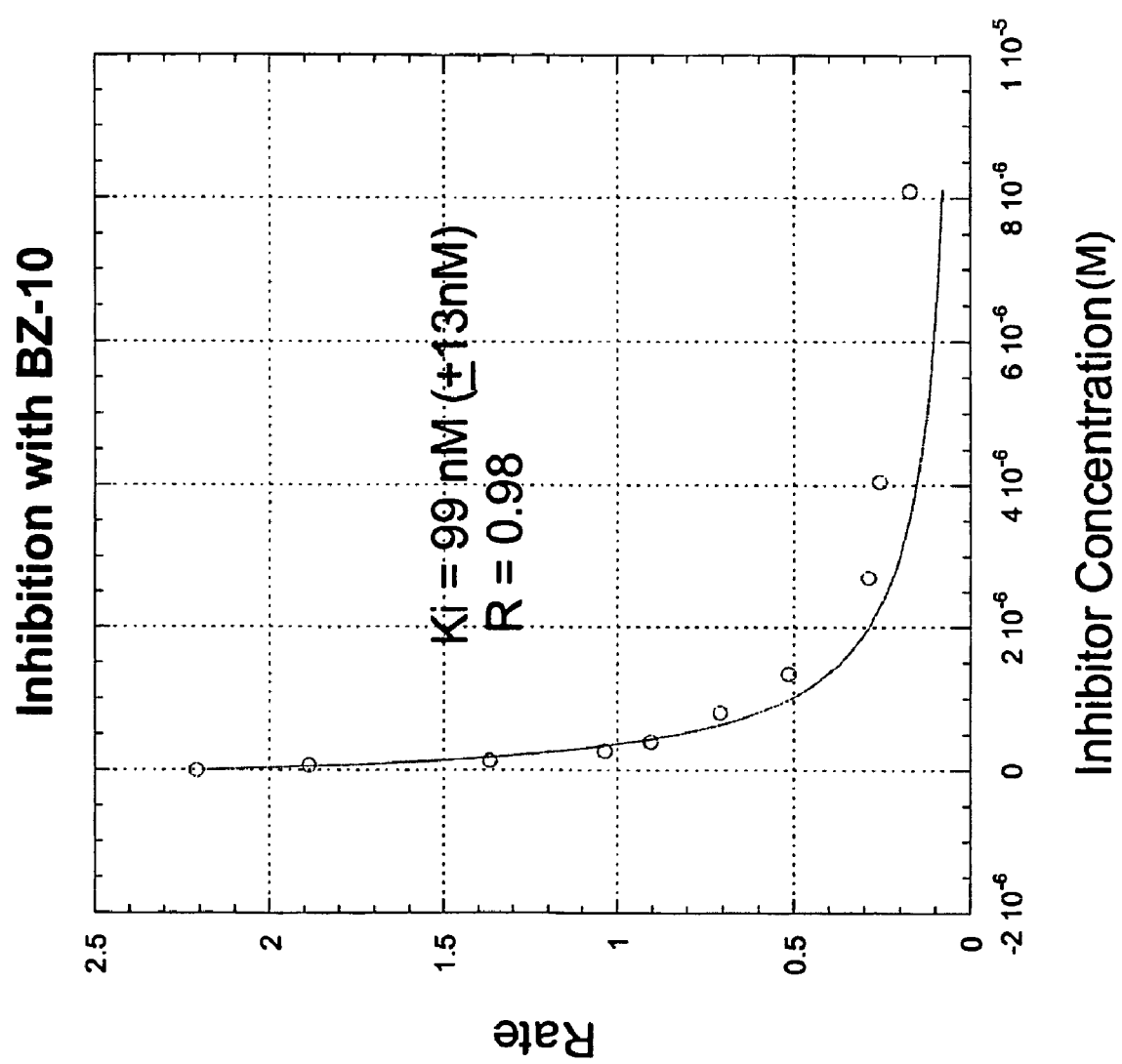
FIG. 10 is a graph of the inhibition of RTA with BZ-10, along with the $K_i$ value calculated for that interaction.
Figure 11:
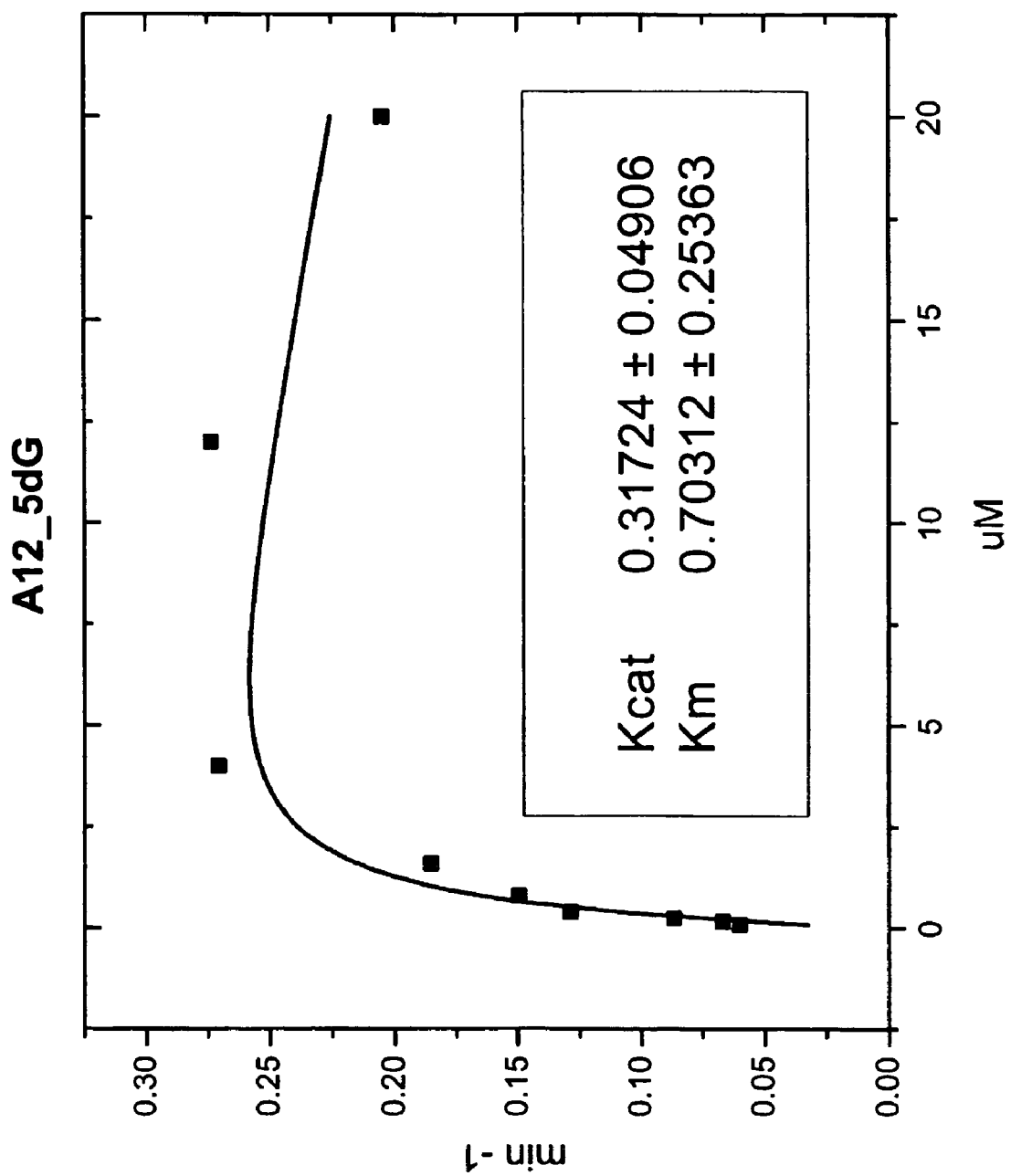
FIG. 11 is a graph of the kinetics of A 12-5dG with RTA, along with calculations of $K_{cat}$ (min-1) and Km (µM) for the reaction.

Inhibition kinetics: Reaction rates were determined in 10 mM sodium citrate buffer (pH 4.0) containing 1 mM EDTA. A-10 was used as the competing substrate and its concentration was 2.5 times above Km. Initial rates were determined in a time representing less than 20% conversion and the adenine release was quantitated by HPLC. The inhibition constant $K_i$ was determined using the equation for competitive inhibition: ($v=k_{cat}*S/(Km*(1+I/K_i)+S)$ where v is the initial reaction rate and S is the substrate concentration. A representative fit to the equation is shown in FIG. 10 for the case of BZ-10. The fits were done using the program Kaleidagraph.

Figure 12:
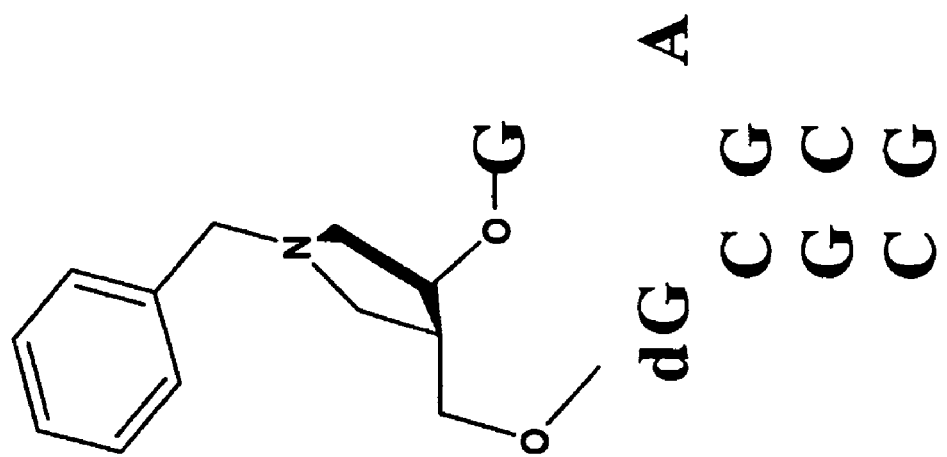
FIG. 12 shows the chemical structure of Nbn-5dG-10.
Figure 13:
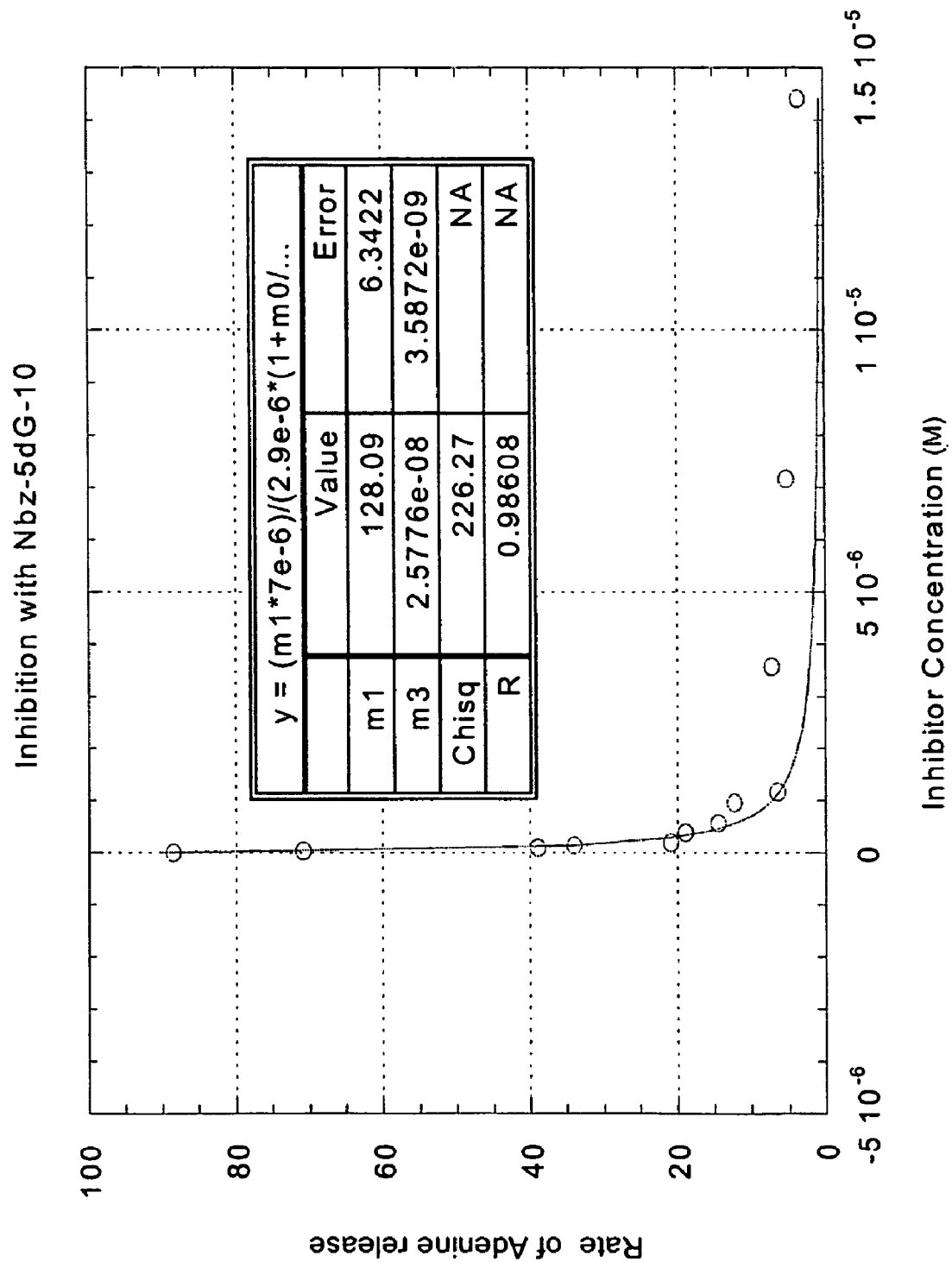
FIG. 13 is a graph of the inhibition of RTA with Nbz-5dG-10.

Inhibition: Gaining affinities at the transition state. The substitution of a deoxyguanosine in the site preceding the depurination site of a small substrate "A12" instead of a guanosine, (i.e. dGAGA instead of GAGA) results in a three fold reduction of $K_{cat}$ while the Km decreased by about 7-8 fold. The reduction in $K_{cat}$ presumably stems from the loss of a hydrogen bond between the 2'-OH of the preceding guanosine and the N7 of the guanosine that immediately follows the adenosine in the depurination site. (Compare the Km for A12-5dG with that for A-14 in FIG. 6 for instance). Based on this result, we conceived an inhibitor that would contain a 2'-deoxyguanosine (dG) substitution at the site adjacent to the 1-azasugar. This structure is NBz-5dG-10 shown in FIG. 12. The four fold enhanced binding of NBz-5dG-10 ($K_i$~26 nM) over BZ-10 ($K_i$~99 nM) is consistent with eight fold decrease in Km of A12-5dG over the substrate, A12. The increased affinity of this inhibitor may be due to a deoxyguanosine substitution leading to a slightly altered, more favorably bound tetraloop conformation in addition to the enhanced "transition state like" features of the N-benzyl-1-azasugar at the depurination site.

Figure 15:
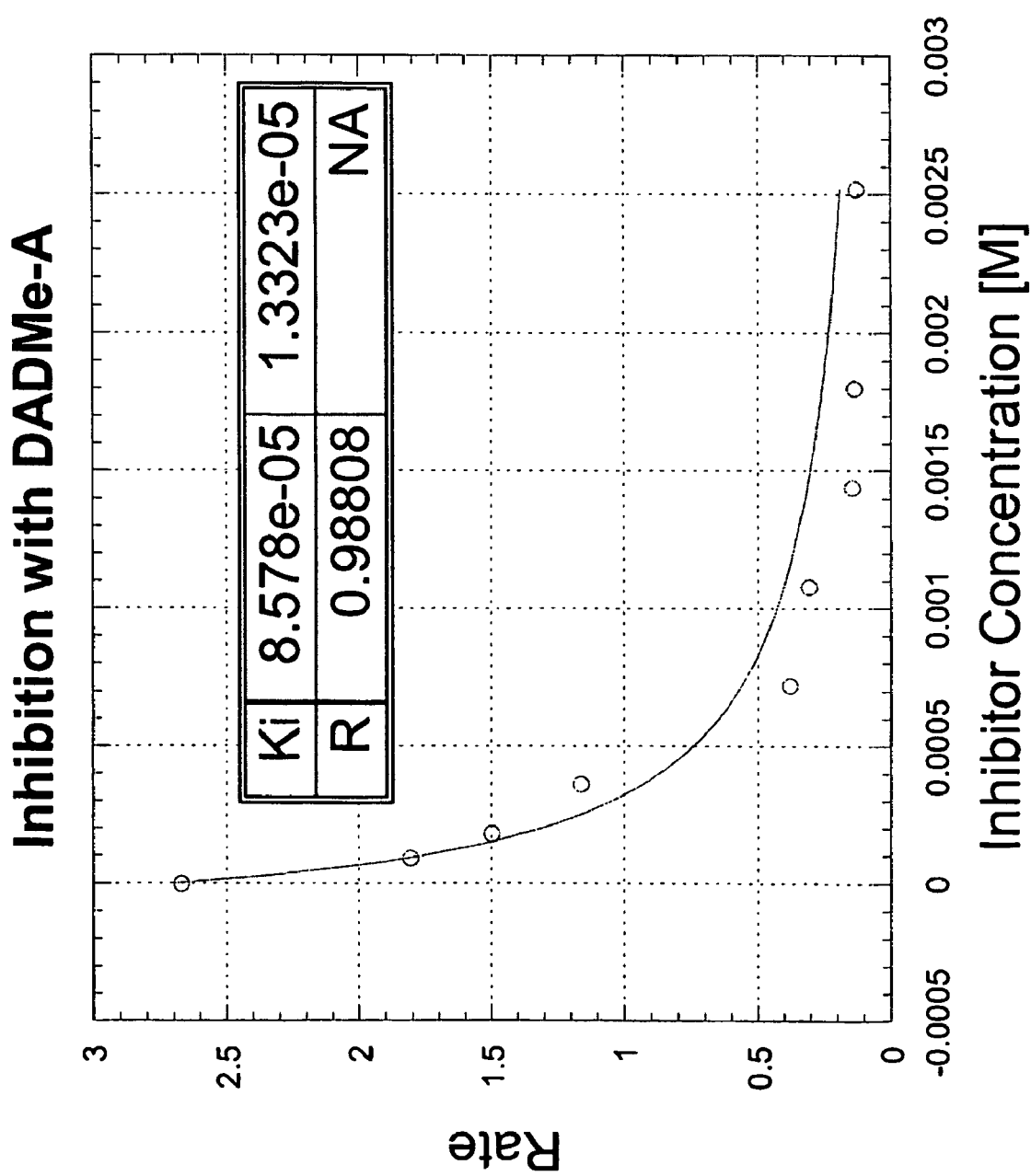
FIG. 15 is a graph of the inhibition of RTA with DADMe-A.

Characterization of small molecule inhibitors of RTA. The pyrrolidine compound, DADMe-A (FIG. 14) was tested as an inhibitor of RTA. The $K_i$ value was found to be 85 μM from competitive assays with A-10 as the substrate (FIG. 15). However, at substrate concentrations >10 times the Km, up to 20% activation was found in the reaction rate at low inhibitor concentrations. This suggests the involvement of two binding sites. At low concentrations, the inhibitor probably binds to the allosteric site in a positively cooperative sense. At high concentrations, however, it binds to the active site and competitively displaces the substrate.

Inhibition was also measured for a ternary complex of RTA, DADMe-A and 9-deazaadenine. 9-Deazaadenine is able to abolish the activation effect suggesting that in the ternary complex, DADMe-A occupies the active site while the purine binds to the second site. The $K_i$ for this ternary complex was 20 μM.

This small molecule approach provides an alternative from the usual oligonucleotide-like inhibitor structures previously developed, and may offer advantages in improved cell entry.

Example 2

Additional Inhibitors of RTA

New second generation azasugars (FIG. 16) were incorporated into stem-loop RNA and used to characterize RTA. Chemical synthesis results in both the 5'- and 3'-termini of oligonucleotides being present as the hydroxyls. Substituents incorporated into the RNA structures are indicated as bold face type and take the place where the ricin-susceptible adenine would be in an analogous stem-loop substrate. These azasugars resemble the oxacarbenium ion transition state proposed in the RTA hydrolytic mechanism. The individual kinetic constants are given in Table 3.

| Inhibitor | $K_i$ (μM) |
|---|---|
| BZ-10 | 0.099 ± 0.013 |
| PZ-10 | 0.163 ± 0.008 |
| PZ-14 | 0.094 ± 0.007 |
| DA-14 | 0.280 ± 0.004 |
| BZ-5dG-10 | 0.026 ± 0.003 |
| PZ-6 | 43 ± 6 |
| PZ-4 | 22 ± 3 |

Table 3. Inhibition Constants for the Inhibitors Provided in FIG. 16

Inhibition Kinetics. Reactions rates were determined in 10 mM potassium citrate buffer (pH 4.0) containing 1 mM EDTA. The total reaction volume was 100 μL. Reactions were started by the addition of RTA at concentrations of 26-48 nM. After incubation of the reaction vials at 37° C. for the allotted time, the reactions were quenched by inactivating the enzyme with 500 mM potassium phosphate buffer (pH 8.3, 100 μL of a 1M solution). The samples were then injected onto a reversed-phase C18 Waters Delta-Pak guard and analytical column (3.9×300 mm) with isocratic elution in 50 mM ammonium acetate (pH 5.0) containing 5% methanol, at a flow rate of 1 mL/min. The enzyme protein is retained on the guard column under these conditions. The extent of RNA hydrolysis by RTA was measured by quantitating the adenine released based on monitoring the peak at 260 nm and a comparison with standards treated with the same protocol. Both substrate and inhibitors were heated to 80° C. for 1 minute, cooled on ice, and incubated at 37° C. for 15 minutes prior to their addition to the assay mix to reduce the variability in the turnover rate that can result from conformational heterogeneity (hairpins vs. other forms) in solution.

In initial rate experiments, the extent of substrate hydrolysis was less than 15%. Product formation was shown to conform to initial rate conditions for the duration of the assay. Values for the inhibition dissociation constant ($K_i$) were determined by fitting the initial rates to the equation for competitive inhibition: $v=k_{cat}S/(S+K_m(1+I/K_i))$, where v is the initial reaction rate, S is the substrate concentration, $K_m$ is the Michaelis constant (2.9 μM for the competitive substrate, A10, under the assay conditions), I is the inhibitor concentration, and $k_{cat}$ is the catalytic turnover at substrate saturation. The concentration range of 7-15 μM used for A10 in this assay represents values that are 2.5-5 times above its $K_m$, and was a convenient range for competitive inhibitor analysis. Inhibitor concentration was kept >5 times that of enzyme except for one case of a strong inhibitor wherein enzyme and inhibitor concentrations were similar when the free inhibitor concentration was determined by the relationship $I=I_t-(1-v_i/v_o)E_t$, where $I_t$ is total inhibitor concentration, $v_i$ and $v_o$ are inhibited and uninhibited steady-state rates, and $E_t$ is total enzyme concentration.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A transition state inhibitor of ricin toxin-A, comprising a stem loop structure that comprises the sequence (d)GX(d)GA, wherein (d)G is either G or dG, wherein at least one of the (d)G moieties is a dG, and wherein X is an adenosine analog of the transition state of ricin toxin-A, wherein X is

[chemical structure] , [chemical structure] or [chemical structure]

wherein ( ) represents the point of attachment to (d)G; or a tautomer thereof, or a pharmaceutically acceptable salt thereof, or an ester thereof, or a prodrug thereof.

2. The transition state inhibitor of claim 1, comprising the sequence C(d)GX(d)GAG.

3. The transition state inhibitor of claim 1, comprising the sequence CGC(d)GX(d)GAGCG (SEQ ID NO:2).

4. The transition state inhibitor of claim 1, comprising the sequence CGCGC(d)GX(d)GAGCGCG (SEQ ID NO:3).

5. The transition state inhibitor of claim 1, comprising a sequence selected from the group consisting of CGCdGX-GAGCG (SEQ ID NO:4), CGCGXdGAGCG (SEQ ID NO:5), and CGCdGXdGAGCG (SEQ ID NO:6).

6. The transition state inhibitor of claim 1, wherein X is

[chemical structure]

wherein ( ) represents the point of attachment to (d)G.

7. The transition state inhibitor, or tautomer, pharmaceutically acceptable salt, ester, or prodrug thereof, of claim 1 in a pharmaceutically acceptable excipient.

8. The transition state inhibitor of claim 1 wherein a further nucleotide sequence extended from the sequence (d)GX(d)GA comprises a sequence of the stem loop structure flanking A4324 of the rat 28S rRNA.

9. A transition state inhibitor of ricin toxin-A, comprising an adenosine analog (X) and stem loop structure that comprises at least 9 ribonucleotides having the sequence CGCGXGAGCG (SEQ ID NO:1) and a sequence of the stem loop structure flanking A4324 of the rat 28S rRNA, and wherein X is selected from the group consisting of

[chemical structure] , [chemical structure] and wherein ( ) represents the point of attachment to the ribonucleotide, or a tautomer thereof, or a pharmaceutically acceptable salt thereof, or an ester thereof, or a prodrug thereof.

10. The transition state inhibitor, or tautomer, pharmaceutically acceptable salt, ester, or prodrug thereof, of claim 9 in a pharmaceutically acceptable excipient.

11. A transition state inhibitor of ricin toxin-A, comprising the sequence (d)GX(d)GA, wherein (d)G is either G or dG and X is an adenosine analog of the transition state of ricin toxin-A, wherein at least one of the (d)G moieties is a dG, and wherein X is wherein ( ) represents the point of attachment to (d)G; or a tautomer thereof, or a pharmaceutically acceptable salt thereof, or an ester thereof, or a prodrug thereof.

12. The transition state inhibitor of claim 11, consisting of CGCdGXGAGCG (SEQ ID NO:4), wherein X is wherein ( ) represents the point of attachment to dG or G.

13. The transition state inhibitor of claim 11, comprising the sequence C(d)GX(d)GAG.

14. The transition state inhibitor of claim 11, comprising the sequence CGC(d)GX(d)GAGCG (SEQ ID NO:2).

15. The transition state inhibitor of claim 13, comprising the sequence CGCGC(d)GX(d)GAGCGCG (SEQ ID NO:3).

16. The transition state inhibitor of claim 11, comprising a sequence selected from the group consisting of CGCdGX-GAGCG (SEQ ID NO:4), CGCGXdGAGCG (SEQ ID NO:5), and CGCdGXdGAGCG (SEQ ID NO:6).

17. The transition state inhibitor, or tautomer, pharmaceutically acceptable salt, ester, or prodrug thereof, of claim 11 in a pharmaceutically acceptable excipient.

18. The transition state inhibitor of claim 11 wherein any further nucleotide sequence extended from the sequence (d)GX(d)GA comprises a sequence of the stem loop structure flanking A4324 of the rat 28S rRNA.

* * * * *